(12) United States Patent
Klein

(10) Patent No.: US 8,417,544 B2
(45) Date of Patent: Apr. 9, 2013

(54) RESEARCH COLLABORATION SYSTEM

(76) Inventor: Jeffrey Alan Klein, San Juan Capistrano, CA (US)

( * ) Notice: Subject to any disclaimer, the term of this patent is extended or adjusted under 35 U.S.C. 154(b) by 242 days.

(21) Appl. No.: 12/894,015

(22) Filed: Sep. 29, 2010

(65) Prior Publication Data

US 2011/0077959 A1    Mar. 31, 2011

Related U.S. Application Data

(60) Provisional application No. 61/246,952, filed on Sep. 29, 2009.

(51) Int. Cl.
*G06Q 10/00* (2012.01)

(52) U.S. Cl.
USPC .................................... 705/2; 705/3

(58) Field of Classification Search ............... 705/2
See application file for complete search history.

(56) References Cited

U.S. PATENT DOCUMENTS

2003/0208378 A1* 11/2003 Thangaraj et al. ............ 705/2
2008/0221921 A1*  9/2008 Love et al. .................... 705/2
2008/0270420 A1* 10/2008 Rosenberg ................ 707/10

* cited by examiner

*Primary Examiner* — Hiep V Nguyen

(74) *Attorney, Agent, or Firm* — James W. Hill; Nathan S. Smith; McDermott Will & Emery LLP

(57) ABSTRACT

Systems and methods for conducting collaborative research are described. In some embodiments, a portal provided on a server allows users, who may be isolated from each other, to network and collaborate on initiating, designing, implementing, analyzing, and/or publishing research.

8 Claims, 3 Drawing Sheets

RESEARCH COLLABORATION SYSTEM

RELATED APPLICATION

This application claims the benefit of U.S. Provisional Application No. 61/246,952, titled "RESEARCH COLLABORATION SYSTEM," filed on Sep. 29, 2009, the entire specification of which is incorporated herein by reference.

FIELD

The present invention relates to research collaboration systems.

BACKGROUND

Many useful clinical trials needed to answer important questions are not performed because there is a financial disincentive to perform clinical trials having a significant likelihood of demonstrating that an expensive therapy is unnecessary. Single-site and multicenter clinical trials are also disincentivized when the cost of making them well controlled and sufficiently powered is high, in terms of required work effort, clinician experience, and funding. Furthermore, important clinical trials will not be funded by pharmaceutical or medical device corporations if there are insufficient financial incentives to do so.

SUMMARY

Therefore, there is a need for systems and methods to facilitate collaborative research, to conduct more efficient and less costly clinical trials, and to enable multiple clinicians more easily to initiate and complete multicenter collaborative clinical trials, in some cases mirroring multiple independent trials that are later analyzed retrospectively, e.g., via meta-analysis or an analogous statistical approach.

In one aspect, a method for conducting collaborative research is disclosed. The method comprises displaying, at a portal, a request for a protocol for at least one clinical trial that investigates a clinical phenomenon, and receiving, over a network, from at least one user, an indicator of at least one suggested protocol responsive to the request. The method also comprises, after a preferred protocol is chosen from among the at least one suggested protocol, displaying, at the portal, an indicator of the preferred protocol, and displaying, at the portal, a request for trial centers to perform at least one preferred clinical trial according to the preferred protocol. The method further comprises, after a plurality of selected trial centers is chosen to perform the at least one preferred clinical trial, displaying, at the portal, an indicator of identity of each of the plurality of selected trial centers. The preferred protocol comprises at least one mandatory clinical parameter whose value must be determined according to the preferred clinical trial and a plurality of optional clinical parameters whose value is optionally to be determined in the preferred clinical trial. The method further comprises receiving clinical trial data from the plurality of selected trial centers based on the preferred protocol. The clinical trial data received from a first of the selected trial centers comprises (a) a value of at the least one mandatory clinical parameter, and (b) a value of at least one of the optional clinical parameters, and the clinical trial data received from a second of the selected trial centers comprises (a) a value of at the least one mandatory clinical parameter, but does not include (b) a value of at the least one of the optional clinical parameters. The method further comprises, using data from each of the plurality of trial centers, including (a) the values of the at least one mandatory parameter received from the first and second trial centers, and (b) the value of the least one of the optional parameters received from the first trial center, performing a meta-analysis to determine a result comprising at least one of an effect size and a variability with respect to at least one of the mandatory parameters.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

DETAILED DESCRIPTION

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

Figure 1:
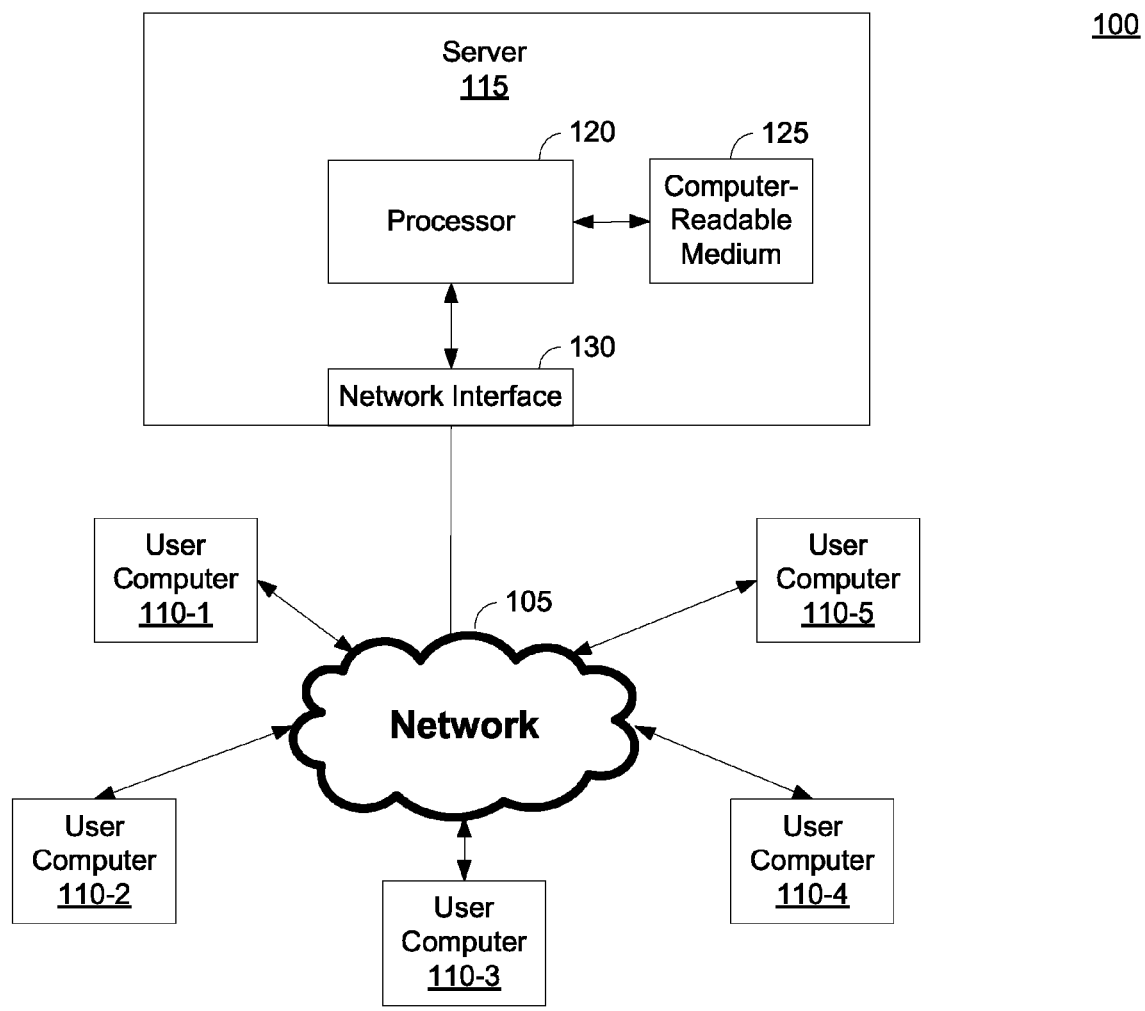
FIG. 1 shows a communication system according to an embodiment of the invention.

FIG. 1 shows a communication system 100 that may be used to implement various embodiments of the invention discussed below. The communication system 100 comprises a plurality of user computers 110-1 to 110-5 and a server 115 that may communicate with each other over a network 105 and the server 115. The user computers 110-1 to 110-5 may include desktops, laptops, smart phones, or other computing device that is able to communicate with the network 105. The network 105 may include the Internet, a cellular network, a Public Switch Telephone Network (PSTN) or a combination thereof. The server 115 may include one or more computers that support a web portal or website that facilitates collaborative research among users at the user computers 110-1 to 110-5, as discussed further below. Each user computer 110-1 to 110-5 may communicate with the server 115, e.g., using an IP address or domain name associated with the server 115. Each user computer 110-1 to 110-5 may download information (document, webpage, etc.) from the server 115 over the network 105 and upload information (document, message, etc.) to the server 115 over the network 105.

The server 115 may include a network interface 130, a processor 120 and a computer-readable medium 125. The network interfaces 130 interfaces the server 115 to the network. The processor 120 is configured to perform various functions of the server 115 discussed below according to embodiments of the present invention. The processor 120 may be implemented with one or more general-purpose and/or special-purpose processors, including, for example, microprocessors, microcontrollers, DSP processors, etc.

The computer-readable medium 125 may be used to store information (e.g., data uploaded to the server from the user computers 110-1 and 110-5) that is accessible by the processor 120. The computer-readable medium 125 may also store a computer program including instructions that are executed by the processor 120 to perform the various functions of the server 115 discussed below. The computer-readable medium 125 may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The computer-readable media 120 may comprise a number of software modules stored thereon. The software modules may include instructions that when executed by the processor 120 cause the processor 120 to perform various functions of the server 115 discussed below.

The server 115 may support a website or web portal that users at the different user computers 110-1 and 110-5 can access over the network 105. In one embodiment, a user may submit a request to research a particular disease to the server 115 through the respective user computer 110-1 to 110-5, and the server 115 may post the request on the website so that users at other user computers 110-1 to 110-5 accessing the server 115 over the network 105 can view the request. For example, the user may be a physician who treats patients in Africa suffering from papillomas (skin warts), caused by human papilloma virus (HPV), and wants to find other users (e.g., physicians) interested in researching papillomas. In this example, the user may submit a request to research papillomas to the server 115, and the server 115 may post the request on the website for other users to view. The request may also include the identity, location, and/or contact information (e.g., e-mail address) of the user submitting the request. The request may include a request for a clinical trial to test the efficacy of a proposed treatment for the disease. For example, the proposed treatment may involve a new use of an existing drug to treat the disease, e.g., an off-label use of a drug approved by the FDA to treat another disease. For the example of papilloma, an existing drug to be considered for an off-label use may be pimercrolimus, which is FDA-approved for topical treatment of eczema. In this embodiment, the request may also include the number and/or demographics of patients that the user has access to for testing the treatment.

Another user who is interested in the research after viewing the request may, for example, click on a link on the website using his/her computer 110-1 to 110-5 indicating an interest in the research. In response, the server 115 may send a webpage to the respective user computer 110-1 to 110-5 requesting the interested user to submit certain information to the server 115 through the user computer 110-1 to 110-5. The requested information may include the identity, location, and/or contact information (e.g., e-mail address) of the interested user (e.g., physician, sponsor, hospital administrator, etc.). The requested information may also include the role the interested user wishes to play in the research. For example, the interested user may be a sponsor who is interested in helping fund the research. As another example, if the research involves testing the efficacy of a proposed treatment, then the interested user may be interested in taking part in a multi-center clinical trial to test the efficacy of the treatment (e.g., set up one of the clinical trial centers for the multicenter clinical trial). In this example, the requested information may also include the number and/or demographics (e.g., age, ethnicity, geographic location, etc.) of patients that the interested user (e.g., physician) has access to for testing the treatment.

The interested user may also submit other information to the server such as background information (e.g., experience of the interested user with patients suffering from the disease), resources (e.g., facilities, equipment, assistants) that are available to the interested user, etc.

After receiving information from one or more interested users in response to the request, the server 115 may post a portion and/or all of the information received from the one or more interested users on the website. For example, the server 115 may post a summary of each interested user responding to the request on a webpage. Each summary may include the identity, location, and/or contact information (e.g., e-mail address) of the interested user (e.g., physician), the number and/or demographics of patients that the interested user has access to, and the role the user is interested in playing in the research (e.g., sponsor the research, set up a clinical trial center, etc.). Each summary may also include the resources (e.g., facilities, equipment, assistants) that are available to the interested user. The summary for each interested user may be generated by the server 115 from the information received from the user. The summaries of the interested users may allow a user viewing the webpage on his/her computer 110-1 to 110-5 to quickly determine certain information, for example, who is interested in the research, how many users are interested in the research, locations of interested users, potential sponsors of the research, etc. Each summary may include a link to additional information about the respective interested user (e.g., background information).

The server 115 may also generate summary information based on information collected from a plurality of interested users, and post the summary information on the webpage. For example, the server 115 may add the number of patients received from each of the plurality of users to obtain a total number of patients, and post the total number of patients on the website. The total number of patients indicates the potential sample size that can be used for a clinical trial if the interested users pool their patients together. The server 115 may also break down the total number of patients by demographics (e.g., age, ethnicity, geographic location, etc.).

The server 115 may also support an online forum allowing interested users at the respective user computers to communicate with one another through online messaging, an online video conferencing, etc. Interested users may also contact each other directly using the contact information provided by the website. Thus, the online forum and contact information provided by the website allow users interested in the research to communicate with one another, for example, to exchange ideas of how to conduct the research, how to obtain funding for the research, how to find others who may be interested in participating in the research, etc.

Thus, the server 115 allows a user (e.g., physician) interested in researching a particular disease to initiate the research by submitting a request to research the disease to the server 115 from the respective user computer 110-1 to 110-5. The user can then find other users (e.g., physicians, sponsors, etc.) who are also interested in the research based on users responding to the request and network with the other user through the website provided by the server 115. The users may be geographically dispersed. For example, a user (e.g., physician) treating patients in Africa suffering from papilloma may submit a request for a clinical trial to test the efficacy of pimercrolimus to treat papilloma. In this example, another user (e.g., physician) treating patients in India suffering from papilloma may view the request on the webpage and respond to the request by offering to set up a clinical trial center using his/her patients. Thus, the users in Africa and India can pool their patients together to increase the sample size of the clinical trial.

In one embodiment, the interested users may wish to collaborate on a clinical trial to test the efficacy of a proposed treatment for the disease (e.g., new use of an existing drug to treat the disease). In this embodiment, one or more of the users may draft a protocol for the clinical trial, and upload the protocol from the respective user computer 110-1 to 110-5 to the server 115 for inspection by other users. The protocol may specify clinical parameters for conducting the clinical trial. For example, the clinical parameters may specify characteristics of patients to receive the treatment and the control patients. The characteristics may be designed to exclude certain patients from the clinical trial including patient with certain preexisting conditions, patients in certain age groups, etc. Pre-existing conditions of a patient may be determined based on the medical history of the patient and/or performing a physical on the patient. The clinical parameters may also include a dosing schedule for patients receiving the treatment including dosage of the drug (e.g., ml of drug per kg of body weight) and the frequency at which the drug is to be administered to the patient.

The clinical parameters may also include the methodology for measuring the efficacy of the drug including the type of measurements to be performed and the measurement schedule. For the example of papilloma, the clinical parameters may specify that the size of the skin lesion be measured with a caliper in units of millimeters. Other types of measurements that may be performed include measuring the patient's temperature, blood pressure, respiration rate, heart rate, etc. The measurement schedule may specify that the patient is to be measured once before receiving treatment to obtain a baseline measurement, the frequency (e.g., once a week) at which the patient is to be measured after and/or during treatment, and/or the time period (e.g., six months) over which the progress of the patient is to be measured.

A user may consider the information on the website in designing a protocol. For example, the user may decide not to include a clinical parameter in the protocol if the inclusion of the clinical parameter would exclude too many patients from participating in the clinical trial, resulting in a sample size that is too small. This determination may be made based on the number of patients and/or demographics of the patients that are potentially available for the clinical trail, which may be posted on the website, as discussed above.

In one embodiment, the draft protocol may include a consent form for patients participating in the clinical trial. Further, the protocol may include at least two types of clinical parameters: mandatory clinical parameters and preferred clinical parameters. A mandatory clinical parameter is a clinical parameter that must be performed by a clinical trial center. An example of a mandatory clinical parameter is that a measurement be performed on a patient at least once before and at least once after the patient receives a treatment. This is because, at a minimum, the patient must be measured before and after the treatment to determine an effect of the treatment. Other examples of mandatory parameters can include weight, height, age, or presence of comorbid conditions, such as obesity, history of myocardial infarction, or hypertension.

A preferred or optional clinical parameter is a clinical parameter that is preferably performed by a clinical trial center, but not required. An example of a preferred clinical parameter is that a measurement be performed on a patient at a frequency of once per week. In this example, a clinical trial center that does not strictly follow the preferred clinical parameter (e.g., only measures the patient once a month) may nevertheless still participate in the clinical trial and submit data for the clinical trial. Other examples of optional parameters, depending on the trial and its clinical intervention, can include weight, height, age, or presence of comorbid conditions, such as obesity, history of myocardial infarction, or hypertension.

In this case, when data from is collected from different clinical trial centers that follow the preferred clinical parameter to varying degrees, a statistical tool may be applied to the data to account for the differences among the clinical trials. The statistical tool may be the same or similar to statistically tools used in conventional meta-analysis to account for differences among different studies. Examples of statistical tools that may be used include simple regression, fixed effect meta-regression, and random effects meta-regression. For example, simple regression may be given by:

$$y_j = \beta_0 + \beta_1 x_{1j} + \beta_2 x_{2j} + \ldots + \epsilon$$

where $y_j$ is the effect size (e.g., effect of treatment) in clinical trial center j, $\beta_0$ is the overall effect size, $x_i$ (i=1, 2 ...) specify different characteristics of the clinical trial and $\epsilon$ specifies the variation between clinical trial centers. Embodiments of the present invention are not limited to the examples above, and any statistical tools known in the art to account for variation among different studies in meta-analysis may also be used in embodiments of the present invention to account for variation among the clinical trial centers.

Conventional meta-analysis is retrospective in the sense that it involves searching literature for past independent studies related to a disease, collecting data from the past independent studies, and analyzing the data to obtain a result (e.g., treatment effect or effect size) and/or a conclusion. Since the past studies are independent from each other, the past studies usually employed different methodologies to obtain their data. Thus, conventional meta-analysis applies a statistical tool to the collected data to account for different methodologies used in the different studies.

In one embodiment of the present invention, the same or similar statistical tools used in conventional meta-analysis to account for variation among different studies may be used to account for variation among the difference clinical trial centers that follow the preferred clinical parameters to different degrees. The meta-analysis according to this embodiment of the present invention differs from conventional meta-analysis in that it is prospective instead of retrospective. As discussed above, conventional meta-analysis is retrospective because it involves collecting data from past independent studies. At the time each past independent study was conducted, it was not known that its data would be pooled together with data from other studies and analyzed with the data from the other studies to obtain results. This embodiment of the present invention is prospective because it is known in advance of conducting the clinical trial that there will be variation among the different clinical trials in the performance of the preferred clinical parameters and that a statistical tool will be used to account for the variation. A preferred clinical parameter allows for differences among the different clinical trial centers because, while preferred, the preferred clinical parameter does not have to be strictly followed by a clinical trial center.

Thus, the protocol may have some flexibility built in by making some of the clinical parameters preferred clinical parameters instead of mandatory. Each clinical trial center may only partially perform a preferred clinical parameter (e.g., measure a patient once a month instead of once a week). Some preferred clinical parameters may not be performed at all. For example, for a clinical parameter specifying that the heart rate of the patient be measured, this clinical parameter may not be performed by a clinical trial center if useable data can still be obtained without this measurement. As discussed above, statistical analysis may later be used to account for variation among the clinical trial centers in following the preferred clinical parameters.

An advantage of having preferred clinical parameters is that it allows the protocol to be flexible. The flexibility of the protocol increases the likelihood that more users will set up clinical trial centers for the clinical trial, and thus, more likely that the clinical trial will get done. This is because a user who is unable to follow some of the preferred clinical parameters (e.g., due to limited resources) may still set up a clinical trial center for the clinical trial. In contrast, a traditional institutional multicenter clinical trial has a rigid inflexible protocol that generally must be uniformly and strictly followed by the trial centers.

In one embodiment, when a proposed protocol for a clinical trial is posted on the website, the server 115 may also post which clinical parameters are mandatory and which clinical parameters are preferred. In this embodiment, a user who is unable to fully comply with one or more of the preferred clinical parameters (e.g., due to limited resources) may still participate in the clinical trial and submit data for the clinical trial. Thus, making some of the clinical parameters preferred instead of mandatory may encourage users with limited resources to set up a trial center for the clinical trial who may otherwise be unable to and/or discouraged from setting up a trail center. While the use of preferred clinical parameters may create variability among the different trial centers based on variations in their adherence to the preferred clinical parameters, the use of preferred clinical parameters increases the number of users able to set up trial centers. This, in turn, increases the number of patients participating in the clinical trial (i.e., the sample size of the clinical trial). The increased sample size increases the statistical power of the clinical trial leading to a greater likelihood that the results of the clinical trial will be statistically significant.

After completing a protocol for the clinical trial, the user may upload the protocol to the server 115. The server 115 may then post the protocol on the website for other user to view and/or download. The server 115 may support an online forum for other users to post comments and/or propose changes to the protocol through their respective user computer 110-1 to 110-5. The user who drafted the protocol may view the comments and/or proposed changes, modify the protocol based on the comments and/or proposed changes, and upload the revised protocol to the server. The server 115 may then post the revised protocol on the website for other users to view. This back and forth may go on until enough users agree on the protocol to conduct the clinical trial.

In one embodiment, a user may agree to a protocol by sending an indication to the server 115 that he/she agrees to the protocol. The server 115 may display the identities of users who have already agreed to the protocol. The server 115 may also determine the total number of patients of users (e.g., physicians) who have agreed to the protocol, and display the total number of patients on the website. The total number of patients of users who have agreed to the protocol may indicate whether the total number of patients (sample size) is sufficient to conduct the clinical trial (which, in essence, comprises multiple smaller clinical trials) or additional patients are needed for the clinical trial (e.g., patients of users who have not yet agreed to the protocol).

In one embodiment, two or more users may each upload different proposed protocols to the server 115 for the clinical trial. In this embodiment, the server 115 may post each of the protocols on the website for other users to view. After reviewing the protocols, the interested users may vote on which one of the protocols they want to adopt for the proposed clinical trial. The clinical trial may be conducted based on the protocol receiving the most votes. The interested users voting on the protocols may include physicians who will set up the clinical trial centers and/or sponsors interested in funding the clinical trial.

After a protocol has been agreed to by interested users, the protocol may be submitted to an institutional review board (IRB) for review by the IRB. Information about one of the users (e.g., experience, qualifications, resources of the user) may also be submitted to the IRB. The IRB review process may be based on the proposed protocol and the information. If the protocol is approved by the IRB in its submitted form or after some modification, then the IRB approved protocol may be uploaded to the server 115 and posted on the website. Other users may then download the IRB approved protocol. For example, one of the users may submit the protocol to the IRB and, after approval by the IRB, send the IRB-approved protocol and/or other related documents to the server 115 for other user to view and download.

Each of the other users may then get IRB approval for that user to set up a clinical trial center using the IRB-approved protocol from the server 115. The IRB may be the same IRB that approved the protocol above or another IRB. To get IRB approval, each of the other users may submit the IRB-approved protocol from the website and information about the user to the respective IRB.

When each user receives IRB approval to set up a clinical trial, the user may submit an indicator to the server 115 indicating that the user has been approved by the respective IRB to set up a clinical trial center. The server may then post a list of users that have received IRB approval from their respective IRBs to set up a clinical trial center. In one embodiment, an interested user acting as a sponsor of the clinical trial may view the list and send funds to one or more of the users that have received IRB approval to set up a clinical trial center.

After receiving IRB approval, a user may set up a clinical trial center and begin collecting data as part of the clinical trial. This may involve the user treating his/her patients suffering from the disease with the proposed treatment and measuring the effects of the treatment according to the protocol. The user may also perform measurements on patients suffering from the disease who do not receive the proposed treatment to provide a control group. As discussed above, in conducting the clinical trial at the respective trial center, the user may only partial perform the preferred or optional clinical parameters specified in the protocol (e.g., based on the resources available to the user). After obtaining data, the user may upload data from the respective user computer 110-1 to 110-5 to the server 105 and the server 105 may post the data on the website for other users to view. Thus, embodiments of the present invention allow users (e.g., physician/clinician) to initiate and/or participate in an IRB-approved multicenter clinical trial.

In one embodiment, one of the preferred or mandatory clinical parameters may involved receiving inputs from the other users not involved in conducting the clinical trial (e.g., the general public). For example, if the clinical trial involves a cosmetic procedure (e.g., face lift), then one of the clinical parameters may involve posting before and after images of a patient receiving the cosmetic procedure on the website and soliciting other users (e.g., general public) on the website to subjectively rate the outcome of the cosmetic procedure (e.g., on a numerical scale) based on the before and after images. The resulting data may be analyzed with other data to obtain results for the clinical trial. An advantage of this embodiment, is that many users may visit the website and submit a rating, thereby increasing the amount of data obtained from the clinical trial.

After the sever 115 has received data from two or more of the users conducting the clinical trial at their respective clinical trial center and/or data from other users (e.g., general public), the data may be forwarded from the server 115 to a statistician for statistical analysis to obtain results from the data. As discussed above, a statistical tool may be applied to the data from the different clinical trail centers to account for variation among the clinical trials centers in following the preferred clinical parameters. After obtaining results from the data, the statistician may upload the results to the server 115 to post the results on the website for review by the users. The results may include an effect size of the proposed treatment compared to the control. For the example of papilloma, the analysis of the data may show a reduction of 60% in the size of the skin lesion for patients receiving the proposed treatment, and a reduction of only 2% for the control patients. In this embodiment, the effect size may be 30. The results may also include variability for the effect size, which may include a variance about a mean or standard deviation. One or more of the users may write an article based on the results, and upload the article to the server 115 to publish the article on the website.

Figure 2A:
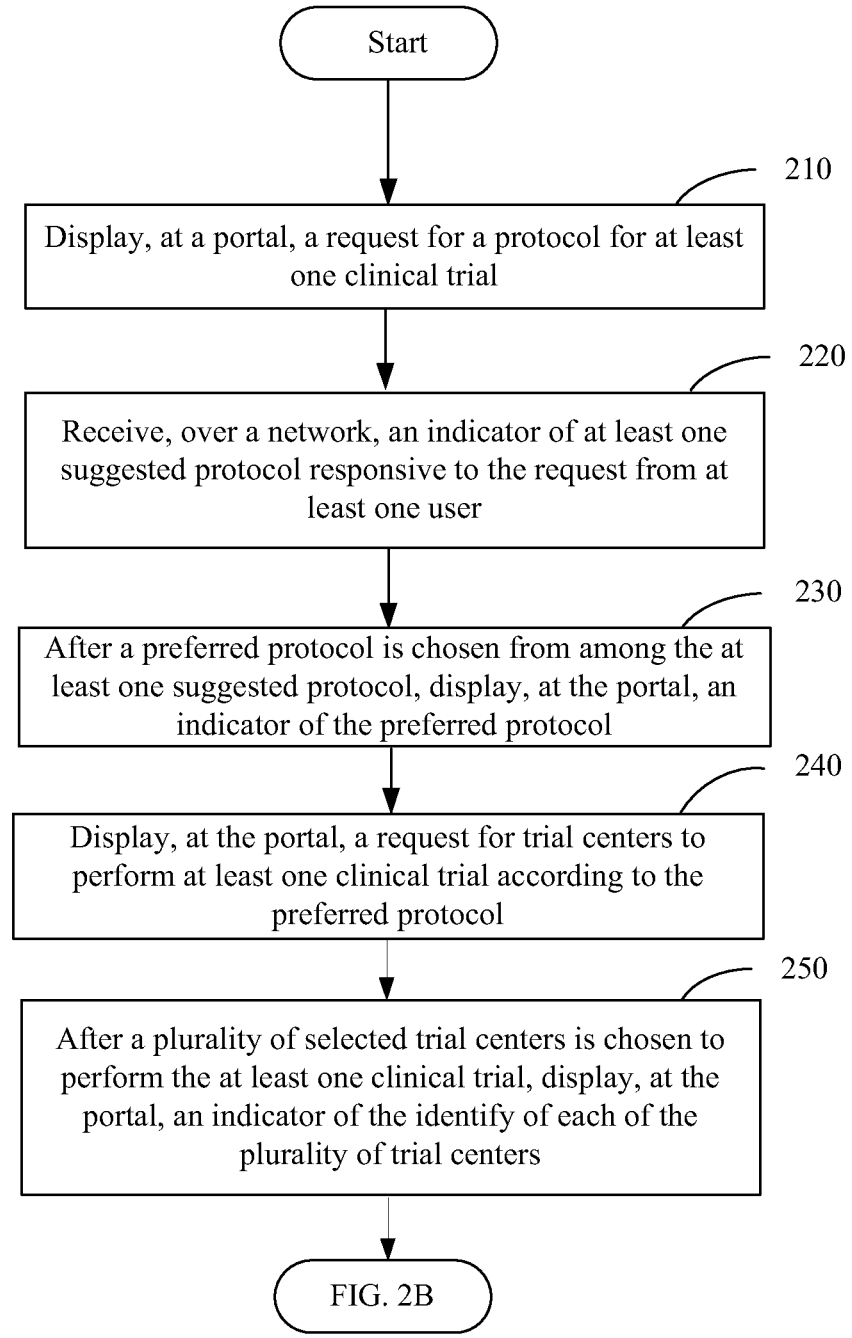
FIGS. 2A and 2B show a flowchart of a method for conducting collaborative research according to an embodiment of the present invention.
Figure 2B:
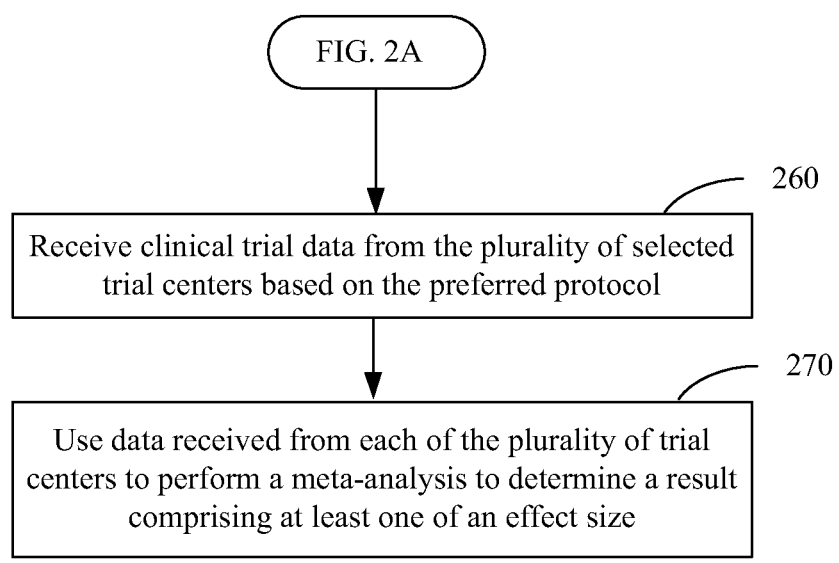

FIGS. 2A and 2B show a method for conducting collaborative research according to an embodiment of the present invention. In step 210, a request for a protocol for at least one clinical trial that investigates a clinical phenomenon is displayed at a portal. The portal may be, for example, a web portal or website provided by the server 115. The request for the protocol may be submitted by a user interested in collaborating with other users to conduct the clinical trial, as discussed above.

In step 220, an indicator of at least one suggested protocol responsive to the request is received over a network from at least one user.

In step 230, after a preferred protocol is chosen from among the at least one suggested protocol, an indicator of the preferred protocol is displayed at the portal.

In step 240, a request for trial centers to perform at least one preferred clinical trial according to the preferred protocol is displayed at the portal.

In step 250, after a plurality of selected trial centers is chosen to perform the at least one preferred clinical trial, an indicator of identity of each of the plurality of selected trial centers is displayed at the portal. The preferred protocol comprises at least one mandatory clinical parameter whose value must be determined according to the preferred clinical trial and a plurality of optional clinical parameters whose value is optionally to be determined in the preferred clinical trial. An example of a mandatory clinical parameter is that a measurement be performed on a patient at least once before and at least once after the patient receives a treatment. An example of an optional clinical parameter is that a measurement be performed on a patient at a frequency of once a week.

In step 260, clinical trial data is received from the plurality of selected trial centers based on the preferred protocol. The clinical trial data received from a first of the selected trial centers comprises (a) a value of at the least one mandatory clinical parameter, and (b) a value of at least one of the optional clinical parameters, and the clinical trial data received from a second of the selected trial centers comprises (a) a value of at the least one mandatory clinical parameter, but does not include (b) a value of at the least one of the optional clinical parameters. For example, when an optional clinical parameter specifies that the patient be measured at a frequency of once a week, the second clinical trial center may omit some of the measurements (e.g., perform a measurement on the patient only once a month instead of once a week). As another example, when the optional clinical parameter specifies that a certain type of measurement be performed on the patient (e.g., heart rate), the second clinical trial center may omit this measurement.

In step 270, data from each of the plurality of trial centers, including (a) the values of the at least one mandatory parameter received from the first and second trial centers, and (b) the value of the least one of the optional parameters received from the first trial center, is used to perform a meta-analysis to determine a result comprising at least one of an effect size and a variability with respect to at least one of the mandatory parameters.

In the above embodiment, the displaying of information on the portal may include making the information accessible on the portal (e.g., posting the information on the website) so that a user can download the information from the server 115 to the respective user computer 110-1 to 110-5 to display the information at the respective user computer.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method for conducting collaborative research, comprising:

displaying, at a portal, a request for a protocol for a clinical trial that investigates a clinical phenomenon;

receiving, over a network, from a user, an indicator of at least one suggested protocol responsive to the request;

after a preferred protocol is chosen from among the at least one suggested protocol, displaying, at the portal, an indicator of the preferred protocol;

displaying, at the portal, a request for trial centers to perform a preferred clinical trial according to the preferred protocol;

after a plurality of trial centers is selected to perform the preferred clinical trial, displaying, at the portal, an indicator of identity of each of the plurality of selected trial centers;

wherein the preferred protocol comprises a mandatory clinical parameter whose value is determined according to the preferred clinical trial;

wherein the preferred protocol comprises a plurality of optional clinical parameters whose value is optionally to be determined in the preferred clinical trial;

after the preferred protocol is chosen, and after each of the selected trial centers has begun the preferred clinical trial according to the preferred protocol, receiving clinical trial data from the plurality of selected trial centers based on (a) the preferred protocol and (b) the preferred clinical trial;

wherein the clinical trial data received from a first of the selected trial centers comprises (a) a value of the mandatory clinical parameter, and (b) a value of at least one of the optional clinical parameters;

wherein the clinical trial data received from a second of the selected trial centers comprises (a) a value of the mandatory clinical parameter, but does not include (b) a value of the at least one of the optional clinical parameters;

using data from each of the plurality of selected trial centers, including (a) the values of the mandatory parameter received from the first and second selected trial centers, and (b) the value of the at least one of the optional parameters received from the first trial center, performing a meta-analysis to determine a result comprising at least one of an effect size or a variability with respect to the mandatory parameter.

2. The method of claim 1, further comprising displaying, at the portal, an indicator of the result.

3. The method of claim 1, wherein the meta-analysis comprises at least one of simple regression, fixed effect meta-regression, or random effects meta-regression.

4. The method of claim 1, wherein a value of at least one of the mandatory or optional parameters is based on an input received from a user.

5. A non-transitory computer-readable medium encoded with a computer program including instructions that are executable by a processor for conducting collaborative research, the instructions including instruction code for:

displaying, at a portal, a request for a protocol for a clinical trial that investigates a clinical phenomenon;

receiving, over a network, from a user, an indicator of at least one suggested protocol responsive to the request;

after a preferred protocol is chosen from among the at least one suggested protocol, displaying, at the portal, an indicator of the preferred protocol;

displaying, at the portal, a request for trial centers to perform a preferred clinical trial according to the preferred protocol;

after a plurality of trial centers is selected to perform the preferred clinical trial, displaying, at the portal, an indicator of identity of each of the plurality of selected trial centers;

wherein the preferred protocol comprises a mandatory clinical parameter whose value is determined according to the preferred clinical trial;

wherein the preferred protocol comprises a plurality of optional clinical parameters whose value is optionally to be determined in the preferred clinical trial;

receiving clinical trial data from the plurality of selected trial centers based on the preferred protocol;

wherein the clinical trial data received from a first of the selected trial centers comprises (a) a value of the mandatory clinical parameter, and (b) a value of at least one of the optional clinical parameters;

wherein the clinical trial data received from a second of the selected trial centers comprises (a) a value of the mandatory clinical parameter, but does not include (b) a value of the at least one of the optional clinical parameters;

using data from each of the plurality of selected trial centers, including (a) the values of the mandatory parameter received from the first and second selected trial centers, and (b) the value of the at least one of the optional parameters received from the first trial center, performing a meta-analysis to determine a result comprising at least one of an effect size or a variability with respect to the mandatory parameter.

6. The computer-readable medium of claim 5, wherein the instructions further comprise code for displaying, at the portal, an indicator of the result.

7. The computer-readable medium of claim 5, wherein the meta-analysis comprises at least one of simple regression, fixed effect meta-regression, or random effects meta-regression.

8. The computer-readable medium of claim 5, wherein a value of at least one of the mandatory or optional parameters is based on an input received from a user.

* * * * *